US008275624B2

(12) United States Patent
Kehoe

(10) Patent No.: US 8,275,624 B2
(45) Date of Patent: Sep. 25, 2012

(54) ELECTRONIC SPEECH AID AND METHOD FOR USE THEREOF TO TREAT HYPOKINETIC DYSARTHRIA

(76) Inventor: Thomas David Kehoe, Boulder, CO (US)

( * ) Notice: Subject to any disclaimer, the term of this patent is extended or adjusted under 35 U.S.C. 154(b) by 304 days.

(21) Appl. No.: 12/577,538

(22) Filed: Oct. 12, 2009

(65) Prior Publication Data

US 2010/0100388 A1 Apr. 22, 2010

Related U.S. Application Data

(60) Provisional application No. 61/105,998, filed on Oct. 16, 2008.

(51) Int. Cl.
*A61F 5/58* (2006.01)

(52) U.S. Cl. .......................................... 704/271; 600/23

(58) Field of Classification Search .......... 704/270–272; 600/23

See application file for complete search history.

(56) References Cited

U.S. PATENT DOCUMENTS 5,961,443 A * 10/1999 Rastatter et al. ................ 600/23
6,754,632 B1 * 6/2004 Kalinowski et al. .......... 704/271

OTHER PUBLICATIONS

Ho, Aileen et al.; Speech volume regulation in Parkinson's disease: effects of implicit cues and explicit instructions; Neuropsychologia; Apr. 1999; pp. 1453-1460.*

Patrick McCaffrey, Ph.D, "Dysarthria: Characteristics, Prognosis, Remediation"; http://www.csuchico.edu/~pmccaffrey//syllabi/SPPA342/342unit14.html.

AM Johnson, PhD, SG Adams, PhD; "Nonpharmacological Management of Hypokinetic Dysarthria in Parkinson's Disease"; Geriatrics & Aging, Feb. 14, 2006, http://www.medscape.com/viewarticle/521623.

Blanchet, Paul; "Treating Fluency and Speech Rate Disorders in Individuals with Parkinson's Disease: The Use of Delayed Auditory Feedback (DAF)," Journal of Stuttering, Advocacy & Research, 1 (2006), p. 83.

Anja Lowit and Bettina Brendel, "The response of patients with Parkinson's Disease to DAF and FSF," Stammering Research, vol. 1., No. 1, Apr. 2004.

Swathi Kiran and Charles R. Larson, "Effect of Duration of Pitch-Shifted Feedback on Vocal Responses in Patients With Parkinson's Disease," Journal of Speech, Language, and Hearing Research, vol. 44, 975-987, Oct. 2001.

Emily Wang and Leo Verhagen, "Improve Speech Using an in-the-Ear Device in Parkinson's Disease (MJFFSpeech)," http://clinicaltrials.gov/ct/show/NCT00488657?order=1.

Jessica Huber, New technology helps Parkinson's patients speak louder, http://www.purdue.edu/uns/x/2009b/090825HuberParkinsons.html, Aug. 25, 2009.

Sadagopan, N., & Huber, J. E. (2007). Effects of loudness cues on respiration in individuals with Parkinson's disease. Movement Disorders, 22, 651-659.

Darling, M. & Huber, J. Changes to Articulatory Kinematics in Response to Loudness Cues in Individuals With Parkinson's Disease. Journal of Speech, Language & Hearing Research, Oct. 2011; 54: 1247-1259.

* cited by examiner

*Primary Examiner* — Abul Azad

(57) ABSTRACT

A speech aid for persons with hypokinetic dysarthria, a speech disorder associated with Parkinson's disease. The speech aid alters the pitch at which the user hears his or her voice and/or provides multitalker babble noise to the speaker's ears. The speech aid induces increased speech motor activity and improves the intelligibility of the user's speech. The speech aid may be used with a variety of microphones, headphones, in one or both ears, with a voice amplifier, or connected to telephones.

20 Claims, 3 Drawing Sheets

ELECTRONIC SPEECH AID AND METHOD FOR USE THEREOF TO TREAT HYPOKINETIC DYSARTHRIA

CROSS REFERENCE TO RELATED APPLICATIONS

This application is a continuation-in-part of copending U.S. provisional patent application No. 61/105,998 filed on Oct. 16, 2008, entitled "Electronic Speech Aid to Treat Hypokinetic Dysarthria Associated with Parkinson's Disease," which is incorporated herein by reference in its entirety.

FIELD OF THE INVENTION

This invention relates, generally, to the field of electronic speech aids, and more specifically to electronic speech aids for use with hypokinetic dysarthria, a speech disorder associated with Parkinson's disease.

BACKGROUND

Hypokinetic dysarthria means "lack of movement articulation disorder." About 98% of cases are associated with Parkinson's disease. It can also be caused by anti-psychotic medications or head injuries. Not all Parkinson's patients experience speech impairment; of Parkinson's patients with speech impairment, not all have hypokinetic dysarthria, e.g., some experience language or cognitive dysfunction (dementia) affecting their speech.

Parkinson's disease is a degenerative disorder of the central nervous system, resulting from decreased stimulation of the motor cortex by the basal ganglia, normally caused by the insufficient formation and action of the neurotransmitter dopamine. Examples of the resulting lack of motor (muscle) movement include a Parkinson's patient thinking that he is moving his legs three feet, but his legs only move three inches. Walking becomes a shuffling gait with short steps and feet barely leaving the ground. Another Parkinson's patient may think she is smiling, but her face is actually an expressionless mask.

Diminished speech motor activity in hypokinetic dysarthria results in decreased vocal volume and in decreased articulation. Speech becomes unintelligible mumbling. Other symptoms of hypokinetic dysarthria include monopitch and monoloudness; pallilalia, or the compulsive repetition of syllables; and "articulatory undershoot" or lack of articulation.

The speaking rate of persons with hypokinetic dysarthria is complex:

> "Bradykinesia (reduced speed of muscles) associated with Parkinson's disease causes difficulty in the initiation of voluntary speech. This can result in delay in starting to talk as well as very slow speech . . . there may be freezing of movement during speech. Rigidity can also occur. Additionally, Parkinson's patients have reduced loudness, imprecise consonant production, reduced pitch variability and festinating speech. The latter can result in extremely fast speech together with short rushes of speech." (Patrick McCaffrey, Ph.D, "Dysarthria: Characteristics, Prognosis, Remediation"; http://www.csuchico.edu/~pmccaffrey//syllabi/SPPA342/342unit14.html).

In other words, hypokinetic dysarthria speech can be both abnormally slow and fast. The patient may start speaking slowly or with difficulty, but then speaking rate accelerates ("festinates") until it is unintelligible.

Parkinson's is typically treated with medications and/or surgery (deep brain stimulation). Medications become less effective as the disease progresses, including less effect on speech. Surgery can improve some symptoms of Parkinson's while making speech worse.

For an overview of treatments for hypokinetic dysarthria, see A M Johnson, PhD, S G Adams, PhD; "Nonpharmacological Management of Hypokinetic Dysarthria in Parkinson's Disease"; *Geriatrics & Aging,* 2006 Feb. 14, http://www.medscape.com/viewarticle/521623).

A variety of voice amplifiers are available, such as the widely used ChatterVox. But these increase vocal volume without increasing clarity, so the result too often is just a louder mumble.

The most widely practiced treatment for speech disorders associated with Parkinson's is Lee Silverman Voice Therapy (LSVT). This speech therapy trains Parkinson's patients to increase vocal volume by increasing respiration activity and vocal fold activity. The result is improved volume and, as a side effect, improved articulation. In general, LSVT is more successful with mild to moderate Parkinson's patients and ineffective with severe patients. LSVT has several limitations. It requires speech motor awareness and control, problems for persons who are losing motor awareness and control. It is also limited by dual-tasking or the problem of thinking about how you're talking at the same time that you're thinking about what you're saying. Dual-tasking is difficult for healthy persons, but the cognitive impairments associated with Parkinson's make LSVT difficult for many Parkinson's patients, and impossible for severe patients.

Pacing boards, with which a user taps a series of squares as she produces each syllable, are sometimes used to help patients speak at a steady speaking rate, but also suffer from the dual-tasking problem. Speech with a pacing board also sounds abnormal.

Delayed auditory feedback (DAF), an electronic device in which the user hears his voice in headphones delayed a fraction of a second, for the purpose of slowing speaking rate, has been tried with Parkinson's patients. A summary of this research concluded that, "results were generally mixed" (Blanchet, Paul; "Treating Fluency and Speech Rate Disorders in Individuals with Parkinson's Disease: The Use of Delayed Auditory Feedback (DAF)," *Journal of Stuttering, Advocacy & Research,* 1 (2006), page 83).

Frequency-altered auditory feedback (FAF), an electronic device in which the user hears her voice in headphones altered in pitch or frequency (i.e., there are two types of FAF), has also been tried with Parkinson's patients. Anja Lowit and Bettina Brendel of Scotland's Strathclyde University found no significant results for +0.5 octave pitch-shifting FAF (shifting the pitch of the users' voices up a half octave) with Parkinson's patients. Six subjects had normal speech intelligibility, and ten subjects had speech scores below the normal range ("low intelligibility group"), but weren't severely impaired (they just were out of the normal range). ("The response of patients with Parkinson's Disease to DAF and FSF," *Stammering Research*, Vol. 1., No. 1, April 2004.)

Another study used changing pitch-shifting FAF with Parkinson's patients to test their ability to alter their vocal pitch when making an "ah" sound. It found Parkinson's patients to be slower than controls when the FAF changed most rapidly. This study didn't investigate whether FAF improved users' speech. (Swathi Kiran and Charles R. Larson, "Effect of Duration of Pitch-Shifted Feedback on Vocal Responses in Patients With Parkinson's Disease," *Journal of Speech, Language, and Hearing Research*, Vol. 44, 975-987, October 2001.)

A study at Rush University Medical Center, initiated Jun. 18, 2007, is testing a device with DAF and FAF with Parkinson's patients (Emily Wang and Leo Verhagen, "Improve Speech Using an in-the-Ear Device in Parkinson's Disease (MJFFSpeech)," http://clinicaltrials.gov/ct/show/NCT00488657?order=1). The device, called SpeechEasy, provides DAF and frequency-shifting FAF. A pilot study found that "Seven of the eight PD patients made significant improvement in their speech, and they were much easier to understand when they used the device." The next phase of the study will test the device with 120 patients.

Jessica Huber, a speech-language pathologist at Purdue University, found that "multitalker babble noise" (similar to twenty unintelligible conversations in a room) increased Parkinson's patients' vocal volume 10 dB. She plans to develop a wearable electronic device that switches on this noise when the user talks. ("New technology helps Parkinson's patients speak louder," http://www.purdue.edu/uns/x/2009b/090825HuberParkinsons.html, Aug. 25, 2009).

There is a need for an invention to induce persons with hypokinetic dysarthria to speak with increased speech motor activity, with the result that their speech is more intelligible, without devoting mental effort to speech motor activities that are normally automatic and unconscious.

SUMMARY

To achieve the foregoing and other objects and in accordance with the purpose of the present invention broadly described herein, one embodiment of this invention comprises a user wearing a headset with a microphone and headphones, or a miniature cellphone earset with a microphone and earphone, which is plugged into a small electronic device that delays and alters the frequency of the user's voice in the user's headphones or earphones.

The small electronic device may alter the frequency of the user's voice by pitch shifting or by frequency shifting (this difference is explained below in the Description).

The device is especially effective with pitch shifting set for more than one-half an octave up.

The device also provides multitalker babble noise to induce a user to speak louder. The multitalker babble noise can automatically adjust to decrease in volume as the user increases his vocal volume, as a form of biofeedback to train increased speaking volume.

The device is especially effective when used with headphones or earphones for both ears, but some users are able to achieve sufficient results with sound to only one ear.

The device plugs into telephones, enabling the user to speak clearly on telephone calls, while hearing a caller's voice in the headphones.

The device includes a variety of anti-background noise features, so that the device can be used in noisy environments such as restaurants. These features include a noise-canceling microphone, a push-to-talk button (especially useful when the user is in a group of people and is mostly listening and occasionally talking), a voice-operated switch to switch the altered auditory feedback sound on when the user speaks and off when the user stops speaking, and filters to remove sound above and below the user's vocal range.

The device can be used wirelessly with a Bluetooth cellphone earset or FM hearing aids or magnetic induction (telecoil) hearing aids.

DRAWINGS

These and other features, aspects, and advantages of the present invention will become better understood with reference to the following description, appended claims, and accompanying drawings, where:

DESCRIPTION

Figure 1:
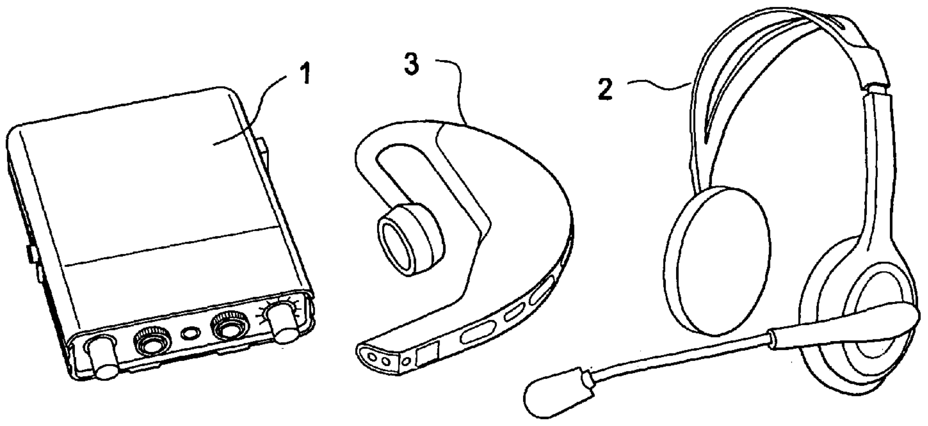
FIG. 1 is a perspective view of a SmallTalk speech aid, an embodiment of the electronic speech aid to treat hypokinetic dysarthria, measuring 7.5×6×1.75 cm (3"×2.25"×0.75") and weighing 80 grams (2.8 ounces), shown with a Sennheiser PC131 headset and a Jabra BT5020 Bluetooth wireless monaural earset.

The present invention uses a combination of delayed auditory feedback (DAF) and frequency-altered auditory feedback (FAF), and/or multitalker babble noise, to induce Parkinson's patients with hypokinetic dysarthria to immediately speak clearly. No training or increased mental effort is needed, an important feature for persons with cognitive impairment.

In accordance with the present invention, a user speaks into a microphone and hears his or her voice in headphones (the term headphones is used here to also include earphones, hearing aids, or similar devices). The microphone and headphones connect to an electronic device that delays and alters the pitch of the user's voice.

The DAF delay is user-adjustable, typically between 25 and 250 milliseconds (ms). As an example of one possible implementation, the Holtek HT8972 digital signal processing computer chip provides delays for voice instruments.

The FAF pitch shift can be adjusted for individual users. Many users find a one-octave upshift (+1 octave) most effective. Greater pitch shifts make the auditory feedback less intelligible to the user, while lesser pitch shifts tend to be less effective (i.e., speech is less intelligible to the listener).

An independent clinical study conducted at the Parkinson's & Movement Disorders Center of Maryland by Leslie Kessler, SLP-CCC; Nancy Solomon, Ph.D., and Stephen Grill, M.D., investigated the SmallTalk? device of the present invention? with six Parkinson's patients, ages 58-65. The study lasted six months and required wearing the devices every day, during all waking hours. The two most cognitively challenged subjects didn't complete the study (using a different headset and wearing the device fewer hours in the day may have been better for these two subjects). Two other subjects reported improved speech with the device, but independent judges didn't rate recordings of these subjects' speech as improved. The last two subjects reported improved speech and independent judges rated their speech as 21 and 32 points better (on a 100-point scale). A different analysis found that three subjects had more intelligible speech. These three subjects have continued using the devices for two years after completing the six-month study. Of these three subjects, "one user was about to be forced into retirement and another had lost his job because of dysarthria." The devices have enabled these two men to continue working. +0.4, +0.6, +0.8, and +1.0-octave FAF settings were tested; the most effective FAF settings were +0.8 octaves for two of the four subjects, and +1.0 octaves for the other two subjects.

Comparison to the Lowit and Brendel Study

The present invention differs in several ways from the device and method used in the Lowit and Brendel study, which found no significant results.

First the Lowit and Brendel study selected subjects with normal speech intelligibility or mild speech impairment and evaluated changes in festination, or rate of speech. The present embodiment is effective for increasing speech motor activity, rather than speech speed, for moderately to severely impaired users.

Second, Lowit and Brendel set their devices for frequency shifts of +0.5 octaves. The present invention has adjustable pitch set individually for each user, and many users find the device to be most effective with frequency shifts of around +1 octave.

Third Lowit and Brendel didn't specify what headsets were used. High-quality microphones and headphones, such as those used in the present invention, can make a difference in device effectiveness.

Comparison to the Wang Study

This embodiment differs in several ways from the ongoing Wang study.

The SpeechEasy device in the Wang study provides frequency-shifting FAF. The present embodiment uses pitch-shifting FAF. The difference is explained below.

The SpeechEasy device in the Wang study provides sound to one ear. The present embodiment provides sound to both ears.

SpeechEasy anti-stuttering devices have a frequency range of 200 to 8000 Hz. Their frequency response isn't flat but instead has a 5-10 dB peak around 3000 Hz. SpeechEasy devices can't reproduce the low range of human voices, especially the fundamental frequency of phonation (125 Hz in adult males) that's key to speech therapy. In contrast, the present embodiment has a flat frequency response (equal volume at all frequencies) from 60 to 6000 Hz.

The SpeechEasy device performs poorly in situations with background noise, because it lacks a noise-cancelling microphone.

No results are known from the Wang study.

Headset Selection

In accordance with the present invention, the user wears a headset 2 (headphones with a microphone, FIG. 1) connected to a small speech processing device 1 (FIG. 1).

Figure 2:
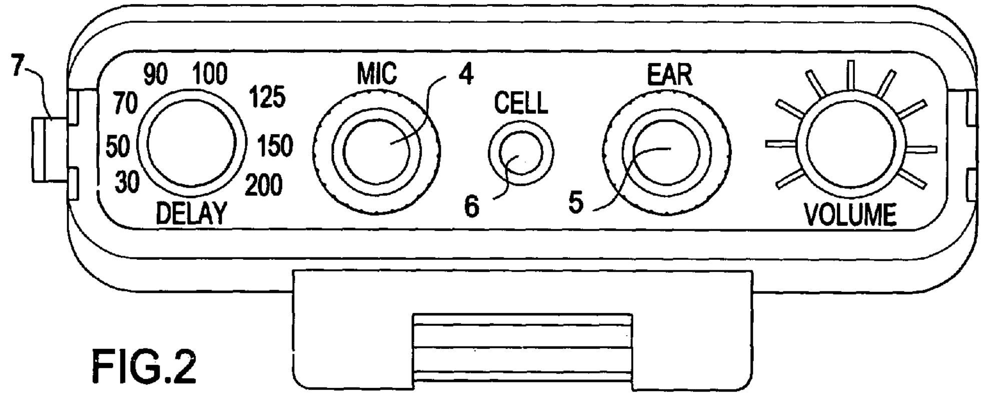
FIG. 2 is a plan view of the end panel of the SmallTalk speech aid, showing the standard 3.5 jacks for microphone and earphones, and a standard 2.5 mm cellphone earset jack.

This embodiment provides a standard 3.5 mm microphone jack 4 (FIG. 2), a standard 3.5 mm headphone jack 5 (FIG. 2), and a standard 2.5 mm cellphone earset jack 6 (FIG. 2). Any standard microphone, headphones, headset, cellphone earset, etc. can be used. Binaural (two ears) sound can be more effective than monaural (one ear) sound.

Because hypokinetic dysarthria includes low vocal volume, a high quality noise-cancelling directional microphone, which picks up the user's voice without picking up background noise, is preferred.

Many users prefer using a Sennheiser PC131 headset 2 (FIG. 1), which has binaural (two ears) headphones and a built-in boom noise-cancelling microphone. Even users with severe motor impairment are able to put on and take off this large headset without help.

Other users prefer a less conspicuous headset, such as a Plantronics MX100S miniature binaural wired cellphone earset, or a Jabra BT5020 Bluetooth wireless miniature monaural cellphone earset 3 (FIG. 1). In general, smaller headsets, especially hearing aids, have worse sound quality, pick up more background noise, are more difficult for impaired persons to handle, and are less effective.

The microphone signal is amplified using a microphone amplifier, for example, the first stage of a Holtek HT8972 audio delay computer chip. This chip is preferred because it has a microphone amplifier, a digital audio delay, and dynamic expansion (see "Anti-Background Noise Features," below). The delayed auditory feedback (DAF) is adjustable by the user.

FAF Pitch-Shifting vs. Frequency-Shifting

The delayed signal then goes through a pitch shifting computer chip, for example, a Yamaha YSS-222D. This chip can shift the pitch up or down, from 0 to 1.4 octaves, in 0.1-octave steps. The pitch shift is adjustable by the user.

FAF can be implemented in two ways. A preferred embodiment uses pitch shifting, changing the pitch of the user's voice up or down on an octave scale. E.g., at +1 octave pitch shift, a 100 Hz signal becomes 200 Hz, a 200 Hz signal becomes 400 Hz, a 400 Hz signal becomes 800 Hz, etc. At −1 octave, an 800 Hz signal becomes 400 Hz, a 400 Hz signal becomes 200 Hz, etc.

The alternative method is frequency shifting, which adds or subtracts a fixed frequency to the signal. E.g., with a 500 Hz addition, a 100 Hz signal becomes 600 Hz, a 200 Hz signal becomes 700 Hz, a 400 Hz becomes 900 Hz, etc. Frequency shifting is inferior to pitch shifting because it produces huge upshifts from lower frequencies, making speech unintelligible; and small, possibly imperceptible upshifts at high frequencies, reducing effectiveness. Frequency shifting is even worse for subtractive or downshifting. E.g., a 200 Hz signal can't be shifted down using a 500 Hz shift, as 200 minus 500 is nothing. Frequency downshifting of speech signals acts much like a filter cutting off much of the vocal range. Frequency shifting uses less computing resources than pitch shifting (frequency shifting doesn't even need a computer, as it can be accomplished using a ring modulator circuit, widely used since the 1950s) so is used on more primitive devices.

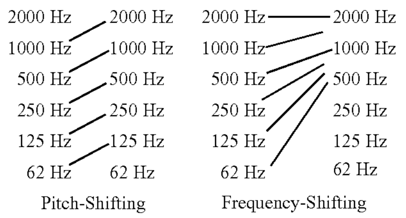

The pitch-shifted signal then goes to a power amplifier, for example, a National Semiconductor LM4881. The signal's volume is controllable by the user, and then goes to the headphone jack and out to the user's headphones.

Multitalker Babble Noise Features

The Lombard effect is the involuntary tendency of speakers to increase their vocal volume when speaking in a situation with loud background noise. AAF (such as the combination of DAF and FAF) alone may result in the opposite of the Lombard effect, i.e., when you hear your voice loudly and clearly you drop your vocal volume. The use of AAF with Parkinson's patients results in clear but quiet speech.

"Multitalker babble noise" consists of twenty persons reading different passages, the result being similar to twenty unintelligible conversations in a room. When Parkinson's patients hear multitalker babble noise they increase their vocal volume 10 dB.

Combining AAF and multitalker babble noise might result in both increased clarity and increased volume, but combining the two effects can also diminish the effectiveness of both, e.g., the multitalker babble noise makes it harder to hear the AAF. One solution to this problem is to filter the multitalker babble noise to provide only low frequency noise, e.g., below 250 Hz, and set FAF at one-octave up, so that an adult male with a 125-Hz fundamental vocal frequency hears his voice above 250 Hz.

Another solution is to use a variable gain amplifier (VGA) with the multitalker babble noise. As the user's voice gets louder, the multitalker babble noise becomes quieter. At first, when the user is speaking quietly, he hears loud multitalker babble noise and quiet AAF. The multitalker babble noise induces him to speak louder, resulting in the AAF becoming louder in his headphones, and the multitalker babble noise becoming quieter. When he is speaking loudly and clearly he hears only AAF. In this embodiment the output of the microphone amp (for example, the first stage of the Holtek HT8972 audio delay computer chip) is fed through an inverting op-amp, and then into an amplifier, such as the voltage-gain pin of a National Semiconductor LMN6505 variable gain amplifier, before mixing with the AAF signal and going to the power amplifier and the headphones.

Another problem with multitalker babble noise is that you don't want to hear it when you're not talking, as it interferes with your hearing. To solve this problem, Jessica Huber used a voice-activated switch worn on the user's throat to switch the multitalker babble noise on when the user talked, and off when the user stopped talking (the opposite of the variable gain amplifier solution, i.e., in Huber's embodiment the multitalker babble noise is loud when the user is speaking loudly and clearly, but the sound is off when the user is not speaking or speaking too quietly for the voice-activated switch to function). Voice-activated switches sometimes don't work well with Parkinson's patients, who sometimes can't make a sound or can speak only very quietly. Also, some people dislike wearing a large sensor switch on their necks, with a wire going to an electronic device, and more wires going to earphones. An alternative solution is to have a manually operated push-to-talk button. Either way, the result is that the user's hearing is unimpaired when he isn't talking; when talks he hears loud multitalker babble noise and FAF; this induces him to speak loudly and clearly, and then the multitalker babble noise diminishes in volume and he continues to speak loudly and clearly.

Anti-Background Noise Features

Some speech aids pick up background noise in noisy environments, impairing the user's hearing and also possibly increasing the cognitive requirements. A user shouldn't suffer impaired hearing to gain improved speech. This embodiment includes several anti-background noise features, including a noise-cancelling directional microphone, a push-to-talk button or switch, high and low filters, dynamic expansion, and voice activation.

The noise-cancelling directional microphone picks up the user's voice while rejecting background noise.

Figure 3:
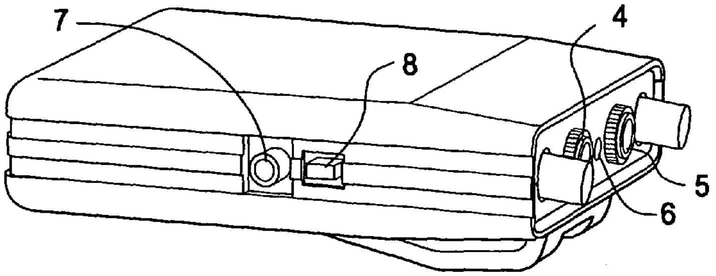
FIG. 3 is a detail perspective view of the side panel of the SmallTalk speech aid, showing the standard 2.5 jacks for interconnection with a telephone and the push-to-talk button for eliminating background noise in noisy environments.
Figure 4:
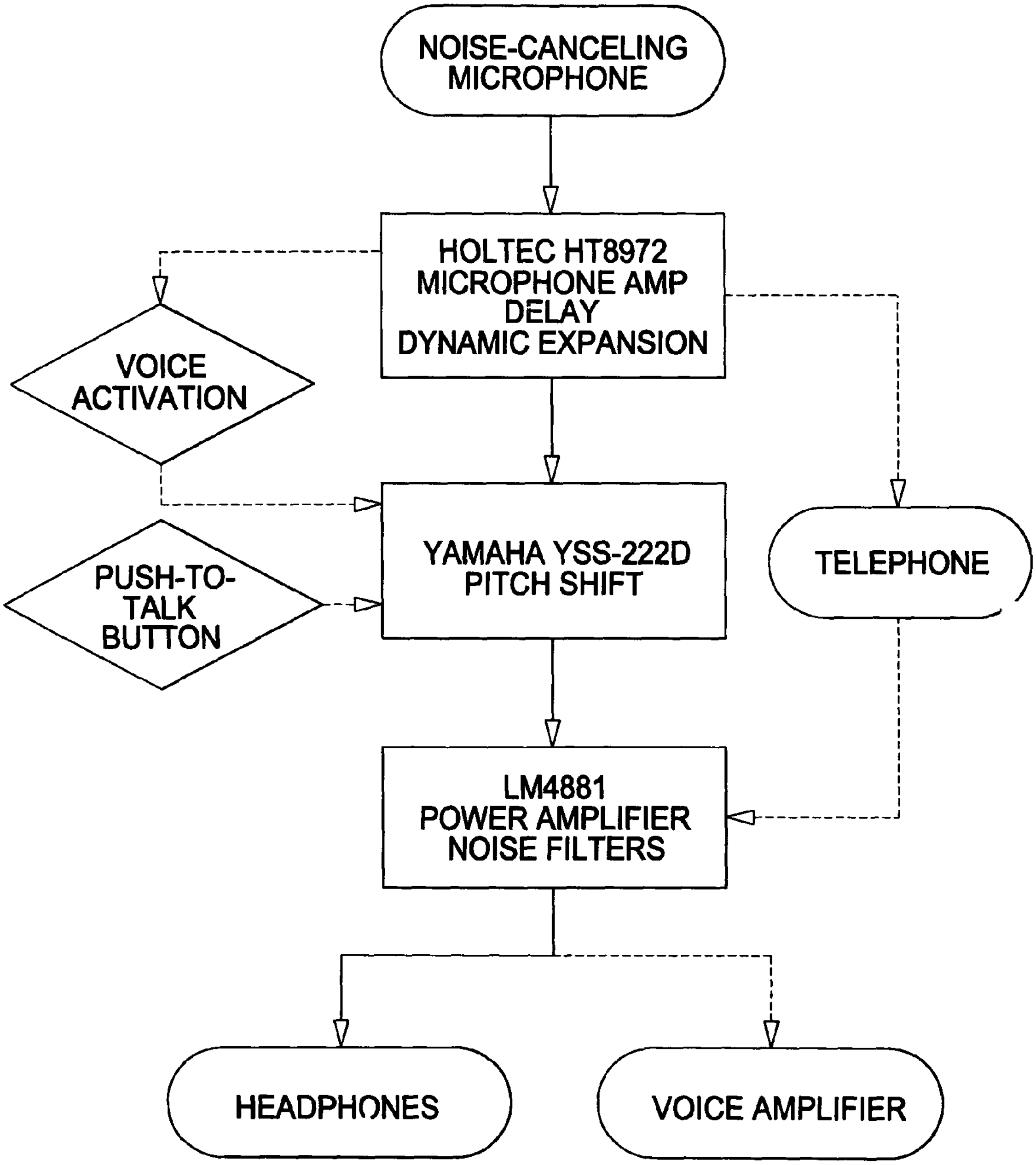
FIG. 4 is a flowchart of device operation in accordance with the present invention.
Figure 5:
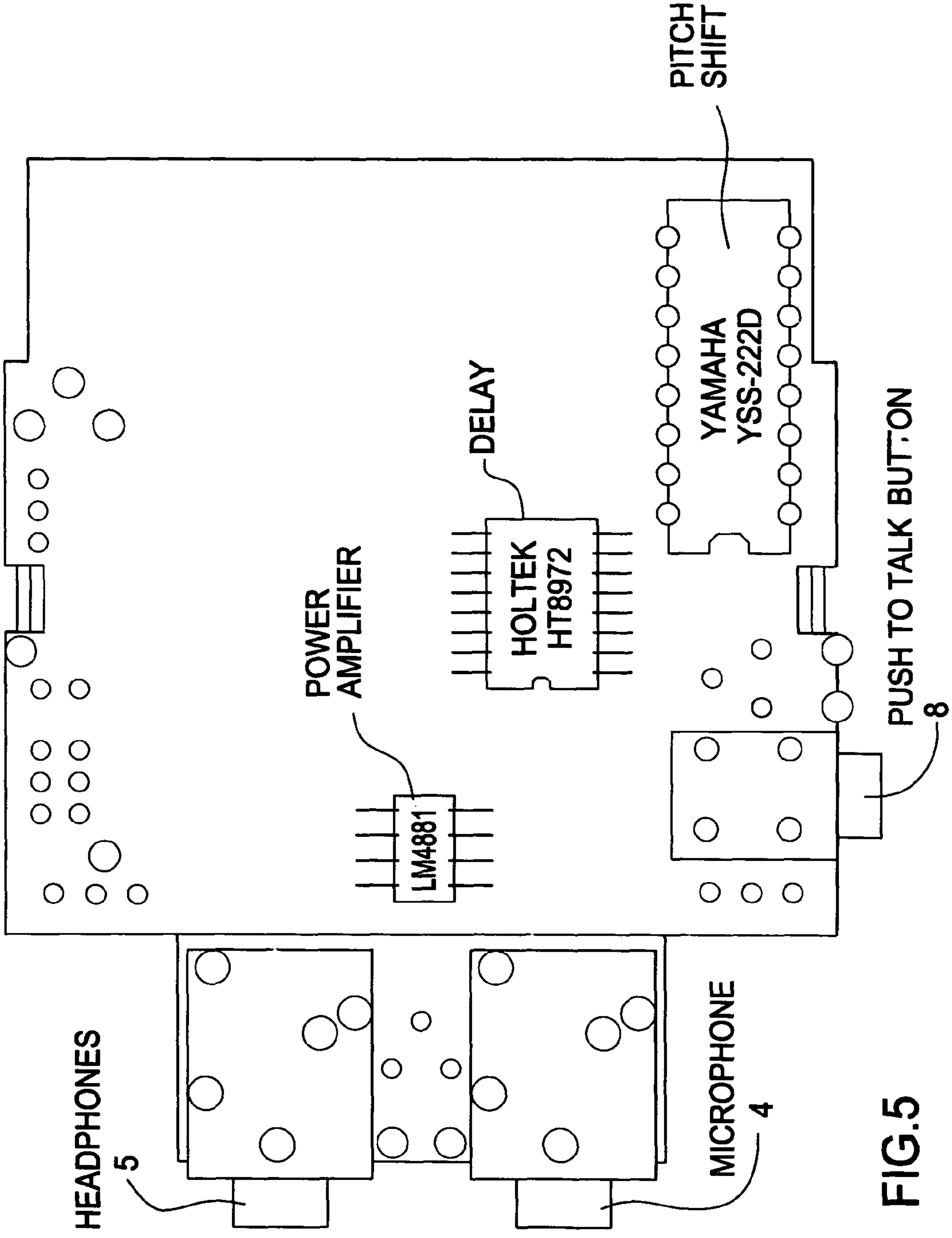
FIG. 5 CAD drawing of the device showing physical placement of principal components.

The push-to-talk button 8 (FIG. 3) enables the user to go out to dinner with friends, have unimpaired hearing while listening to the friends talk, and then push the button and instantly switch the sound on when the user wishes to speak. The push-to-talk feature can be implemented via the "sleep" pin on the Yamaha YSS222-D chip (pin 15).

The high and low filters eliminate background noise above and below the user's vocal range. High and low filters are active resistor-capacitor (RC) type on the HT8972 microphone and output amplifiers, and on the LM4881 power amplifier (three active filters).

Dynamic expansion makes the user's voice louder and background noise quieter. Dynamic expansion can be achieved with a resistor on pin 7 of the HT8972 chip.

Voice activation switches turn sound on automatically when the user speaks, and off automatically when the user stops speaking. Voice activation can be achieved by rectifying the signal from the HT8972 chip, then using a LP339 comparator to switch the YSS222-D chip into or out of sleep mode. A more sophisticated form of voice activation can be achieved by using a National Semiconductor LM2907 frequency to voltage convertor to detect the vocal frequencies of the user's voice, combined with vocal volume, to differentiate the user's voice from loud background noises.

Telephone Interface

Telephones are ideal for using electronic speech aids. A user's weak voice can be amplified. Large, conspicuous devices or headphones aren't visible to callers.

The present invention may include a telephone interface. Preferably, the telephone interface is a standard 2.5 mm headset jack 7 (FIG. 3), with the output of the HT8972 delay chip as the outgoing voice, and the incoming caller's voice feeding into the LM4881 power amplifier. A volume control is provided to amplify the user's outgoing voice if necessary, as well as a separate? volume control to adjust the caller's incoming voice.

Voice Amplification

If listeners need increased vocal volume, such as for public speaking, a voice amplifier, such as a ChatterVox, can be plugged into the headphone jack of the device. The user can plug his earset into the cellphone earset jack, or use headphones and a voice amplifier by employing a Y-adapter (available at Radio Shack, etc.) in the headphone jack.

Wireless Features

Many users prefer to not have wires around their heads, and other embodiments of the present invention have wireless signal transmission.

For example, the Bluetooth wireless protocol can run full duplex, that is, one signal from the microphone to the processing device, and another, simultaneous signal from the processing device to the headphones. Bluetooth also has a long range (about ten meters) and is inexpensive; Bluetooth earsets made for cellphones cost about $100.

Another alternative includes frequency-modulated (FM) radio transmission, used in many hearing aids. The range is further than Bluetooth. However, the signal is only one way, from the processing device to the hearing aid; and the cost is high, typically $1000 for a transmitter and $1000 or more for the hearing aid receiver. FM hearing aids can be used binaurally in an embodiment.

A third wireless alternative is electromagnetic induction transmission to telecoil hearing aids. This is inexpensive and simple; the transmitter costs less than $100 and uses no batteries, and most hearing aids have telecoils, so this alternative can be a good choice for a user who already wears hearing aids. However, the transmission range is short (inches), so the transmitter, which is a large, heavy coil of wire, has to be worn around the neck.

CONCLUSION, RAMIFICATION, AND SCOPE

Thus the reader will see that at least one embodiment of the speech aid provides effective improvement in speech intelligibility, yet minimizes mental effort, for use by persons with all stages and severities of hypokinetic dysarthria.

While my above description contains many specificities, these should not be construed as limitations on the scope, but rather as an exemplification of one preferred embodiment thereof. Many other variations are possible. For example, a general-purpose digital signal processor (DSP) computer chip could be programmed to do the pitch shifting instead of using the single-purpose Yamaha YSS-222D computer chip.

Accordingly, the scope should be determined not by the embodiment illustrated, but by the appended claims and their legal equivalents.

| Comparison of devices | | | | |
|---|---|---|---|---|
| | Lowit and Brendel | Wang | Huber | Kehoe |
| Delayed auditory feedback (DAF) | Yes | Yes | No | Yes |
| Frequency-altered auditory feedback (FAF) | Pitch-shifting, +0.5 octaves | Frequency-shifting | No | Pitch-shifting, 0 to +1.4 octaves |
| Multitalker babble noise | No | No | Yes, voice activated | Yes, automatic volume adjustment |
| Proven effective | Not effective | Pilot study, no data | Pilot study, no data | Yes (clinical study) |
| Number of ears | Two (binaural) | One (monaural) | Two (binaural) | One or two |
| Rejects background noise | | No | Yes | Yes |
| Frequency range | | 200-8000 Hz | | 60-6000 Hz |

What is claimed is:

1. A speech aid for treating speech disorders associated with Parkinson's disease, comprising:
   means for detecting when a user speaks;
   means for detecting when the user stops speaking;
   means for providing noise that induces the Lombard effect to induce the user to speak louder, to one or more of the user's ears when the user speaks, and to terminate said noise when the user stops speaking; and in addition to providing noise; and
   means for providing altered auditory feedback (AAF) to one or more of the user's ears.

2. The speech aid of claim 1, wherein said noise comprises multitalker babble noise.

3. The speech aid of claim 1, wherein said speech disorder is hypokinetic dysarthria.

4. The speech aid of claim 1, wherein said altered auditory feedback (AAF) is selected from the group consisting of delayed auditory feedback (DAF) and frequency-altered auditory feedback (FAF) and combinations thereof.

5. A speech aid for treating speech disorders associated with Parkinson's disease, comprising:
   means for detecting when a user speaks;
   means for detecting when the user stops speaking;
   means for providing noise that induces the Lombard effect to induce the user to speak louder, to two of the user's ears when the user speaks, and to switch off said noise when the user stops speaking.

6. The speech aid of claim 5, wherein said noise comprises multitalker babble noise.

7. The speech aid of claim 5, wherein said speech disorders include hypokinetic dysarthria.

8. The speech aid of claim 5, including means to prevent hearing impairment.

9. The speech aid of claim 8, wherein said means to prevent hearing impairment comprises means for detecting the user's vocal volume, and if said vocal volume is low increases the volume of said Lombard effect-inducing noise, and if said vocal volume is high reduces the volume of said Lombard effect-inducing noise.

10. A speech aid for treating speech disorders associated with Parkinson's disease, comprising:
   means for detecting when a user speaks;
   means for detecting when the user stops speaking;
   means for providing noise that induces the Lombard effect to induce the user to speak louder, to one or more of the user's ears when the user speaks, and to switch off said noise when the user stops speaking; and means for preventing hearing impairment comprising means for detecting the user's vocal volume, and if said vocal volume is low increases the volume of said Lombard effect-inducing noise, and if said vocal volume is high reduces the volume of said Lombard effect-inducing noise.

11. The speech aid of claim 10, wherein said noise comprises multitalker babble noise.

12. The speech aid of claim 10, wherein said speech disorders include hypokinetic dysarthria.

13. A speech aid for treating speech disorders associated with Parkinson's disease, comprising:
   means for detecting when a user speaks;
   means for detecting when the user stops speaking;
   means for providing noise that induces the Lombard effect to induce the user to speak louder, to one or more of the user's ears when the user speaks, and to switch off said noise when the user stops speaking; and means for providing said noise to one or more of a user's ears via a plurality of transducers interconnected wirelessly to said means for providing said noise.

14. The speech aid of claim 13, wherein said wireless interconnection is selected from the group consisting of Bluetooth wireless protocol, frequency modulated (FM) radio, electromagnetic induction, and combinations thereof.

15. The speech aid of claim 13, wherein said noise comprises multitalker babble noise.

16. The speech aid of claim 13, wherein said speech disorders include hypokinetic dysarthria.

17. A speech aid for treating speech disorders associated with Parkinson's disease, comprising:
   means for detecting when a user speaks;
   means for detecting when the user stops speaking;
   means for providing noise that induces the Lombard effect to induce the user to speak louder, to the user when the user speaks, and to switch off said noise when the user stops speaking; and means for connecting said means for providing said noise to a telephone.

18. The speech aid of claim 17, wherein said means to connect said means for providing noise to a telephone comprises:

means for providing the user's voice to a remote party via a telephone; and means for providing the remote party's voice to the user, using the same transducers that provide said noise to the user.

19. The speech aid of claim 17, wherein said noise comprises multitalker babble noise.

20. The speech aid of claim 17, wherein said speech disorders include hypokinetic dysarthria.

* * * * *